US006555125B2

(12) United States Patent
Campbell

(10) Patent No.: US 6,555,125 B2
(45) Date of Patent: Apr. 29, 2003

(54) LESION AND ULCER MEDICATION

(76) Inventor: Phillip Campbell, 2700 Lake Rd., Huntsville, TX (US) 77340

( * ) Notice: Subject to any disclaimer, the term of this patent is extended or adjusted under 35 U.S.C. 154(b) by 0 days.

(21) Appl. No.: 09/982,038

(22) Filed: Oct. 17, 2001

(65) Prior Publication Data

US 2002/0044956 A1 Apr. 18, 2002

Related U.S. Application Data

(63) Continuation-in-part of application No. 09/451,608, filed on Nov. 30, 1999, now Pat. No. 6,352,711.

(51) Int. Cl.[7] .............................. A61F 13/00; A61K 9/14
(52) U.S. Cl. ........................ 424/435; 424/434; 424/485; 424/195.18; 514/925; 514/928
(58) Field of Search ............................ 424/195.18, 434, 424/435, 485; 514/925, 928

(56) References Cited

U.S. PATENT DOCUMENTS

| | | | |
|---|---|---|---|
| 4,765,983 A | * | 8/1988 | Takayanagi et al. |
| 4,780,320 A | | 10/1988 | Baker ........................ 424/493 |
| 4,940,587 A | * | 7/1990 | Jenkins et al. |
| 5,081,158 A | * | 1/1992 | Pomerantz |
| 5,446,070 A | | 8/1995 | Mantelle .................. 514/772.6 |
| 5,458,884 A | | 10/1995 | Britton et al. .............. 424/435 |
| 5,578,315 A | | 11/1996 | Chien et al. ................ 424/435 |
| 5,651,987 A | * | 7/1997 | Fuisz |
| 5,658,586 A | | 8/1997 | Rajaiah et al. ............. 424/435 |
| 5,714,165 A | * | 2/1998 | Repka et al. |
| 5,800,832 A | * | 9/1998 | Tapolsky et al. |
| 5,874,479 A | | 2/1999 | Martin ....................... 514/724 |
| 5,955,097 A | * | 9/1999 | Tapolsky et al. |
| 6,283,933 B1 | * | 9/2001 | D'Alessio et al. |

OTHER PUBLICATIONS

Colgate Orabase® Soothe–N–Seal™, package purchased Aug. 23, 2001.

* cited by examiner

*Primary Examiner*—Christopher R. Tate
(74) *Attorney, Agent, or Firm*—Kenyon & Kenyon

(57) ABSTRACT

Pharmaceutical compositions are provided which comprise effective amounts of antimicrobials, anti-inflammatories, and antihistamines, to provide an ulcer medication which prevents secondary infections and promotes healing while providing immediate relief from pain. The composition may be used to treat a variety of ulcers including but not limited to intraoral aphthous ulcers and non-oral lesions. The compositions of the present invention may also be combined with materials capable of forming seals over ulcers or lesions to further promote the healing process.

20 Claims, No Drawings

LESION AND ULCER MEDICATION

This Application is a Continuation-In-Part of application Ser. No. 09/451,608, filed Nov. 30, 1999, which issued as U.S. Pat. No. 6,352,711.

FIELD OF INVENTION

The present invention relates to the field of medications for the treatment of lesions and ulcers, and in particular to medications for treatment of intraoral ulcers. More particularly, the present invention provides a composition and a method for treatment of intraoral ulcers which promotes rapid healing, promotes immediate relief from severe pain, and prevents secondary infections.

BACKGROUND OF INVENTION

An effective cure of intraoral ulcers has been sought by the medical and dental communities without success. There is essentially no known cause or cure of intraoral ulcers. These ulcers can be extremely painful to patients, and generally persist for seven to ten days. Research over the last several decades has not provided any significant answers or treatment regimens.

While the etiologies of oral aphthae, or canker sores, are quite varied, the central concern is the severe pain they cause. This pain affects the quality of life for millions of individuals. It is believed that the pain related to the oral ulcerative lesions is made more severe by the secondary infections caused by the prevailing oral bacteria.

Historically, intraoral ulcers and lesions were treated with chemical cautering techniques, often involving silver nitrate sticks. These methods involve the use of highly caustic substances to cause a scarring of the ulcer or lesion. These methods all shared the common characteristic in that they themselves caused severe pain in the patients. There was concern as to whether the pain caused by these treatments actually exceeded the pain caused by the ulcer or lesion they were intended to treat. Examples of chemical cautering products include Negatan from Savage Laboratories. More recent treatments have similarly involved the use of caustic agents, such as chlorhexidine, the active ingredient in Kanka, an over-the-counter intraoral ulcer medication.

One currently used common treatment for intraoral ulcers is the use of acylovir, an antiviral agent effective in treatment of certain forms of herpes. Acyclovir is available from Glaxo Wellcome under the tradename Zovirax. Zovirax consists essentially of acyclovir in a polyethylene glycol base and is available as an ointment or rinse. This product approaches the problem of ulcers based on the hypothesis that such ulcers or lesions are viral in nature. Another recent treatment is use of a product called Aphthasol, available from the Block Drug Company. Aphtasol consists of amlexanox, an antihistamine, in an adhesive paste. This treatment is based on the hypothesis that oral ulcers and lesions are caused by an autoimmune or allergic response of the body. However, none of the above products has proven to be effective in reliably reducing the pain associated with the ulcer while simultaneously speeding the healing process and preventing secondary infections.

SUMMARY OF THE INVENTION

The present invention is based on the discovery that certain combinations of antimicrobial agents, anti-inflammatories, and antihistamines, along with an accompanying mucoadhesive provide unexpected and highly effective intraoral ulcer medications. The present invention provides an intraoral ulcer medication which prevents both secondary infection and promotes healing while simultaneously providing immediate relief from pain. This ulcer medication comprises an antimicrobial, an anti-inflammatory, an antihistamine, and optional antifungal and anesthetic components along with a mucoadhesive or equivalent.

The antimicrobial component can be any bacteria or microbe resistant compound suitable for intraoral application, including but not limited to Tetracycline HCl and Zinc Oxide. Tetracycline HCl is preferred due to the minimal chance of an allergic reaction due to its use. Tetracycline HCl is a very effective antibiotic for preventing secondary infections associated with intraoral ulcers. Such secondary infections may be due to, but not limited to, *Streptococcus mutans,* a bacteria commonly present in the mouth. Zinc oxide has also been shown to have antimicrobial properties, especially with respect to *Streptococcus mutans,* as well as providing a degree of soothing relief from the pain associated with intraoral ulcers. Zinc Oxide could be used alone, or in addition to Tetracycline HCL, or other antimicrobial agent that is selected. The advantage of Zinc Oxide is its availability as a non-prescription component, which is accentuated where the other components selected share this non-prescription characteristic, as well as its efficacy as an antimicrobial at low concentrations. The other antimicrobial agents which could be selected include, but are not limited, to the various forms of Penicillin based antibiotic/antimicrobial agents.

The antihistamine component can be any antihistamine compound suitable for intraoral application, including but not limited to Diphenhydramine. Diphenhydramine is preferred since it is an effective antihistamine and is available as an over-the-counter drug. The advantage of an over-the-counter component is accentuated where the other components selected share this non-prescription characteristic. The inclusion of an antihistamine in this medication is based on the observation of an allergy etiology with some aphthous ulcers.

The anti-inflammatory component helps promote the healing process for the lesion or ulcer. The anti-inflammatory component can be any steroid, or other form of anti-inflammatory, component suitable for intraoral application, including but not limited to Dexamethasone. Dexamethasone is preferred since it is a particularly effective steroid.

The optional antinfungal component can be any fungal resistant compound suitable for intraoral application.

Additionally, Metronidazole may be particularly useful when used in treatment of intraoral ulcers in patients who are HIV-positive. Metronidazole is preferred due to its efficacy in the treatment of aphthous ulcers. Particularly where the composition is to be used in patients who are HIV-positive, inclusion of an agent such as Metronidazole is recommended.

The addition of an optional topical anesthetic to the composition of the present invention can assist in the decrease of the pain associated with the ulcer or lesion. While the optional anesthetic can be any anesthetic suitable for intraoral application, Benzocaine is preferred. Special care must be taken with use in patients who are allergic to caine derivatives. The optional anesthetic functions to provide immediate relief in situations where the pain from the intraoral ulcer is particularly intense.

The mucoadhesive component can be any mucoadhesive component for intraoral application suitable for intraoral application, including but not limited to Karaya Gum or Orabase. Karaya gum is an effective mucoadhesive, which allows the compound to remain on the lesion. Karaya Gum is preferred due to its inexpensive nature, and its availability in powdered form for use in the powdered medication form.

In the preferred embodiment the medication comprises effective amounts of Tetracycline HCl, Metronidazole, Dexamethasone, Diphenhydramine, Zinc Oxide, and Karaya Gum. A representative example of a possible composition of the preferred embodiment is shown in Example 1 below. In another embodiment, the composition of Example 1 is formed omitting the optional component Metronidazole, keeping all other components the same.

Use of the compound shown in Example 1 on patients has resulted in oral lesions and ulcers disappearing within 72 hours, some within 24 to 48 hours. The pain associated with the ulcer is reported to disappear immediately.

EXAMPLE 1

1. The medication was formed by mixing the following pharmaceutical compounds in powder form:

| Tetracycline HCl | 500 mg |
| --- | --- |
| Metronidazole | 125 mg |
| Dexamethasone | 1 mg |
| Diphenhydramine | 17 mg |
| Zinc Oxide | 67 mg |
| Karaya Gum | 350 mg |

2. The resulting powder is then applied in powder form to the oral ulcer.

3. Application of the powder is repeated two to three times daily until the ulcer has completely healed.

Patients who have been treated in the manner described in Example 1 have reported an immediate soothing effect. Additionally, the ulcers have completely healed in less than 3 days, sometimes in a period as short as under 48 hours. This meets the goals of pain relief and rapid healing time.

The concentrations of the various components can be varied depending upon which characteristics are desired most. The disclosed preparation consists of two portions a first portion which comprises the active ingredients, and a second portion which comprises the mucoadhesive or equivalent. The combination of the first and second portions results in the final disclosed composition. In preferred embodiments, the components of the first portion make up the following weight percent of the first portion:

| Antimicrobial | 25–95% |
| --- | --- |
| Metronidazole (optional) | 5–65% |
| Anti-inflammatory | 0.02–0.7% |
| Antihistamine | 0.5–11% |

Note that the Metronidazole is described as optional. Where no Metronidazole is added, it would comprise zero weight percent of the first portion. Additionally, if an optional anesthetic were added, the weight percent added would be selected based on the efficacy of the selected anesthetic, the amount of pain suffered by the patient, and be selected so as to maintain the weight percent of the other components within the weight percent ranges disclosed above. The second portion, the mucoadhesive portion, comprises between 25 and 60% of the weight of the final compound.

Further variations on the weight percentages are possible without sacrificing the overall beneficial effects of the composition. For example, it has been found that even at low levels zinc oxide provides an effective antimicrobial/bacteriostatic effect, thereby reducing the overall weight percent of the antimicrobial component. Further, due to the varied effectiveness of antimicrobials, Metronidazole, antihistamines, and anti-inflammatories, other than those disclosed as preferred above, the actual weight percents used may be different.

In an alternative embodiment, an optional flavoring agent is added to the medication since the tetracycline may produce a bitter taste. Any flavoring agent that is appropriate for intraoral use may be used, specifically the use of peppermint oil and/or saccharine is contemplated.

In an alternative embodiment the medication would be available in an over-the-counter formulation. The medication of this embodiment would comprise a non-prescription antihistamine, antimicrobial, and mucoadhesive. In one embodiment this over-the-counter formulation would comprise Diphenhydramine, Zinc Oxide, and Karaya Gum. In one embodiment the formulation would comprise a first portion consisting of between 5 and 50 weight percent Diphenhydramine, and 50 to 95 weight percent Zinc Oxide, and a second portion comprising Karaya Gum amounting to between 25 and 60 weight percent of the final composition. A representative example of a possible composition of the preferred embodiment is shown in Example 2 below.

EXAMPLE 2

1. A compound porposed for an over-the-counter treatment was formed by mixing the following pharmaceutical compounds in powder form:

| Diphenhydramine | 17 mg |
| --- | --- |
| Zinc Oxide | 67 mg |
| Karaya Gum | 30–125 mg |

2. The resulting powder is then applied in powder form to the oral ulcer.

3. Application of the powder is repeated two to three times daily until the ulcer has completely healed.

The medication of the present invention may advantageously be applied in the form of a powder. A powder prepared in accordance with either Example 1 or Example 2 is "puffed" onto the wet lesion two to three times daily. An appropriate amount of medication is used to coat the entire surface of the lesion. In alternative embodiments, the medication could be provided in the form of a paste, gel, a spray, lozenge, or an oral rinse.

The medication of the present invention may also be used in conjunction with an adhesive such as a cyanoacrylate formulation. Formulations which may be useful include the 2-octyl cyanoacrylate formulation, sold by Colgate-Palmolive under the tradename ORABASE SOOTHE-N-SEAL, and the 2-octyl cyanoacrylate formulation sold by Johnson & Johnson under the tradename DERMABOND. Other cyanoacrylate formulations, including formulations comprising ethyl cyanoacrylate may also be used as part of the present invention. These cyanoacrylate formulations when applied to a lesion create a barrier seal between the lesion and the environment. It has been found that by following application of the medication of the present invention to the lesion with application of a cyanoacrylate liquid protectant, particularly the ORABASE SOOTHE-N-SEAL, significant improvement in lesion healing times is realized as compared to the performance of the medication alone. While the cyanoacrylate formulations used alone may help healing to proceed at a natural rate, combination with the medication of the present invention allows healing to occur at an accelerated rate. The use of materials other than cyanoacrylate formulations which are effective in creating a seal over a lesion in an oral environment also may be used in combination with the medication of the present invention to provide the above described beneficial results.

While the disclosed medication is believed to be especially effective for use with aphthous ulcers, it should be effective with most types of oral lesions. For example, the oral ulcers frequently suffered by individuals who are HIV-positive, while not aphthous, would also be effectively treated by this novel treatment.

Beyond intraoral applications, it is expected that the above medication would provide an effective treatment for non-oral lesions, such as those which are experienced frequently among diabetics. The specific use of dexamethasone and tetracycline HCl, alone or in combination with the other components disclosed above, is expected to be effective for all forms of lesions. For treatment of non-oral ulcers, the addition of karaya gum or other mucoadhesive would be optional.

I claim:

1. A method of treating intraoral ulcers comprising the steps of first combining at least one antimicrobial agent, at least one anti-inflammatory, at least one antihistamine, and at least one mucoadhesive to create a final composition and applying the final composition to the intraoral ulcer, wherein said antimicrobial component comprises between 25 and 95 weight percent of the active ingredients, said anti-inflammatory component comprises between 0.02 and 0.7 weight percent of the active ingredients, and said antihistamine comprises between about 0.5 and 11 weight percent of the active ingredients.

2. A method as in claim 1 wherein the at least one anti-inflammatory is dexamethasone and the at least one antihistamine is diphenhydramine.

3. A method as in claim 2 wherein the at least one antimicrobial agent is chosen from the group consisting of zinc oxide and tetracycline HCl.

4. A method as in claim 1 wherein the final composition comprises 500 parts tetracycline HCl, 1 part dexamethasone, 17 parts diphenhydramine, and 67 parts zinc oxide.

5. A method as in claim 4 wherein the final composition further comprises 125 parts Metronidazole.

6. A method of treating intraoral ulcers and lesions comprising the steps: combining at least one antimicrobial agent, at least one anti-inflammatory, and at least one antihistamine to create a pharmaceutical composition wherein said antimicrobial component comprises between 25 and 95 weight percent of the active ingredients, said anti-inflammatory component comprises between 0.02 and 0.7 weight percent of the active ingredients, and said antihistamine comprises between about 0.5 and 11 weight percent of the active ingredients, applying said pharmaceutical composition to an intraoral ulcer or lesion, and applying an adhesive over the pharmaceutical composition.

7. The method as in claim 6 wherein the adhesive comprises a cyanoacrylate formulation.

8. The method as in claim 7 wherein the cyanoacrylate formulation comprises 2-octyl cyanoacrylate.

9. The method as in claim 7 wherein the cyanoacrylate formulation comprises ethyl cyanoacrylate.

10. The method as in claim 6 wherein the pharmaceutical composition further comprises a mucoadhesive.

11. The method as in claim 10 wherein the anti-inflammatory component is dexamethasone and the antihistamine component is diphenhydramine.

12. The method as in claim 10 wherein the adhesive comprises a cyanoacrylate formulation.

13. The method as in claim 12 wherein the cyanoacrylate formulation comprises 2-octyl cyanoacrylate.

14. The method as in claim 12 wherein the cyanoacrylate formulation comprises ethyl cyanoacrylate.

15. The method as in claim 7 wherein the anti-inflammatory component is dexamethasone and the antihistamine component is diphenhydramine.

16. The method as in claim 6 wherein the anti-inflammatory component is dexamethasone and the antihistamine component is diphenhydramine.

17. The method as in claim 6 wherein said pharmaceutical composition comprises 500 parts tetracycline HCl, 1 part dexamethasone, 17 parts diphenhydramine, and 67 parts zinc oxide.

18. The method as in claim 7 wherein said pharmaceutical composition comprises 500 parts tetracycline HCl, 1 part dexamethasone, 17 parts diphenhydramine, and 67 parts zinc oxide.

19. The method as in claim 8 wherein said pharmaceutical composition comprises 500 parts tetracycline HCl, 1 part dexamethasone, 17 parts diphenhydramine, and 67 parts zinc oxide.

20. The method as in claim 9 wherein said pharmaceutical composition comprises 500 parts tetracycline HCl, 1 part dexamethasone, 17 parts diphenhydramine, and 67 parts zinc oxide.

* * * * *